United States Patent
Morrow et al.

(10) Patent No.: US 9,557,268 B2
(45) Date of Patent: Jan. 31, 2017

(54) ANALYTE DETECTOR AND METHOD

(75) Inventors: Danny Gene Morrow, Redwood City, CA (US); Louis John Dietz, Mountain View, CA (US); Darius Akbar Sadeghi, Carmel, CA (US)

(73) Assignees: GAUGE SCIENTIFIC, LLC, Redwood, CA (US); BIO-CHEK LLC, Carmel, CA (US)

(*) Notice: Subject to any disclaimer, the term of this patent is extended or adjusted under 35 U.S.C. 154(b) by 605 days.

(21) Appl. No.: 13/038,225

(22) Filed: Mar. 1, 2011

(65) Prior Publication Data

US 2012/0223251 A1    Sep. 6, 2012

(51) Int. Cl.
*G01N 21/64* (2006.01)
*G01N 21/27* (2006.01)
*G01N 21/94* (2006.01)
*G01N 33/02* (2006.01)
*G01N 21/84* (2006.01)

(52) U.S. Cl.
CPC ............ *G01N 21/645* (2013.01); *G01N 21/64* (2013.01); *G01N 21/6428* (2013.01); *G01N 21/274* (2013.01); *G01N 21/94* (2013.01); *G01N 33/025* (2013.01); *G01N 2021/8466* (2013.01); *G01N 2201/0221* (2013.01)

(58) Field of Classification Search
USPC .............. 250/252.1, 308, 361 R, 362, 363.1, 369, 250/458.1, 459.1, 580, 909, 910
See application file for complete search history.

(56) References Cited

U.S. PATENT DOCUMENTS

| 5,818,045 | A  | * | 10/1998 | Mark et al. ............... 250/339.12 |
| 7,304,741 | B2 |   | 12/2007 | Sadeghi et al. |
| 7,400,405 | B2 |   | 7/2008  | Sadeghi et al. |
| 2007/0139735 | A1 | * | 6/2007 | Shakespeare et al. ........ 358/509 |
| 2012/0088486 | A1 | * | 4/2012 | Messerchmidt ............. 455/418 |

* cited by examiner

*Primary Examiner* — David Porta
*Assistant Examiner* — Carolyn Igyarto
(74) *Attorney, Agent, or Firm* — Edward S. Wright

(57) ABSTRACT

Instrument and method for detecting pesticides and other analytes. A sample to be tested is mounted on a cassette and inserted into a housing which is substantially impervious to light, and light from a source within the housing is directed toward the sample to induce fluorescent emission from analyte on the sample. Fluorescent emissions from the sample are monitored with a detector within the housing to detect emissions having a spectral content characteristic of the analyte to be detected. Data from the detector is processed, and information based on the processed data is displayed. In some embodiments, the instrument is calibrated with data from a reference sample of known concentration or density. The detector measures the analyte in units of mass per unit area, and in some embodiments the mass per unit area is converted to units of concentration or density of the analyte in the sample.

26 Claims, 4 Drawing Sheets

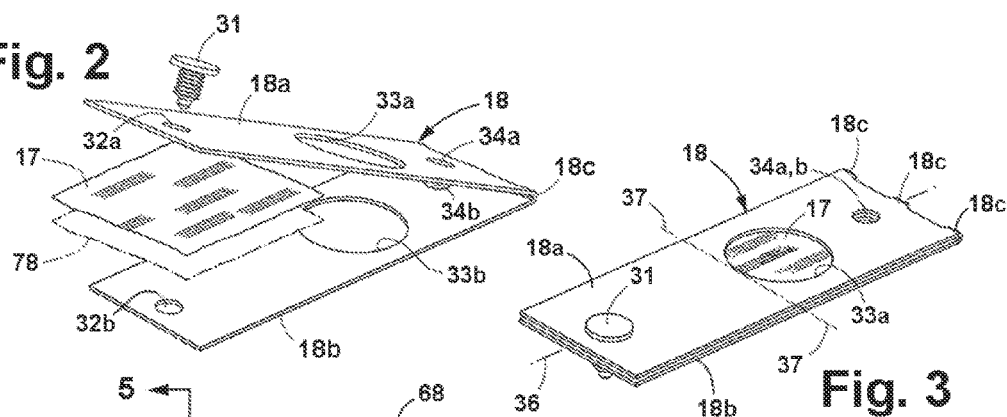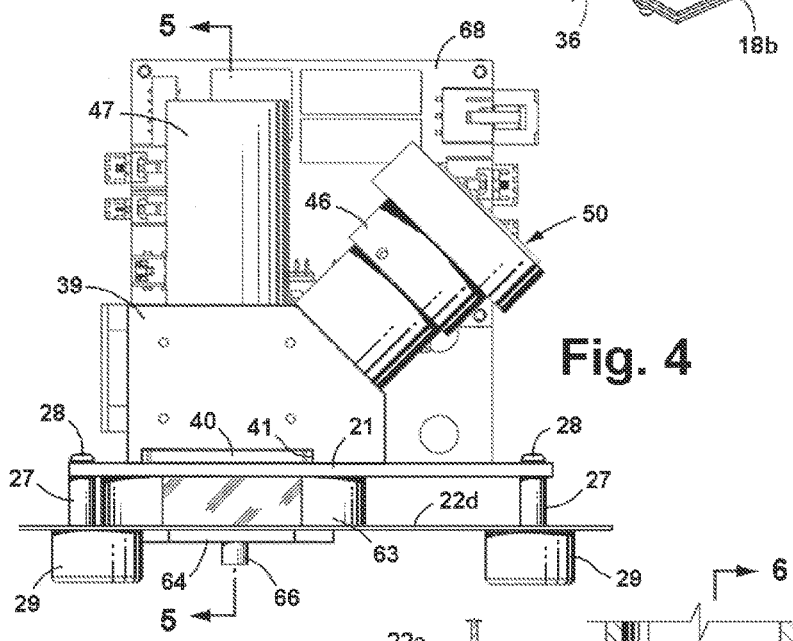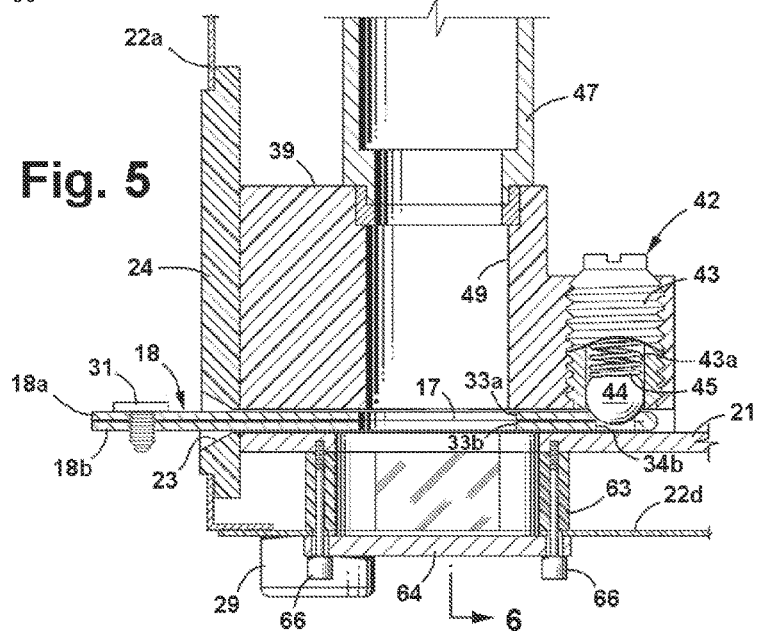

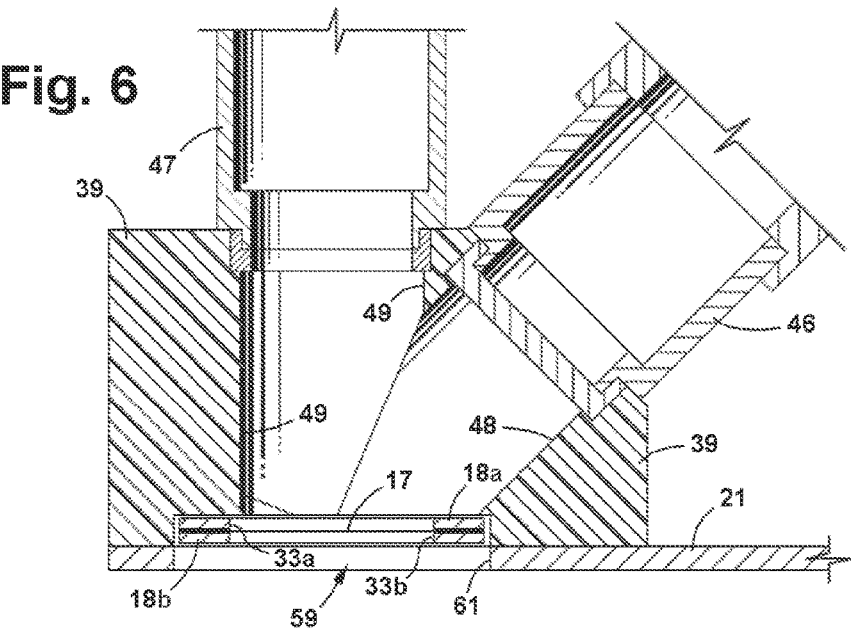
Fig. 6
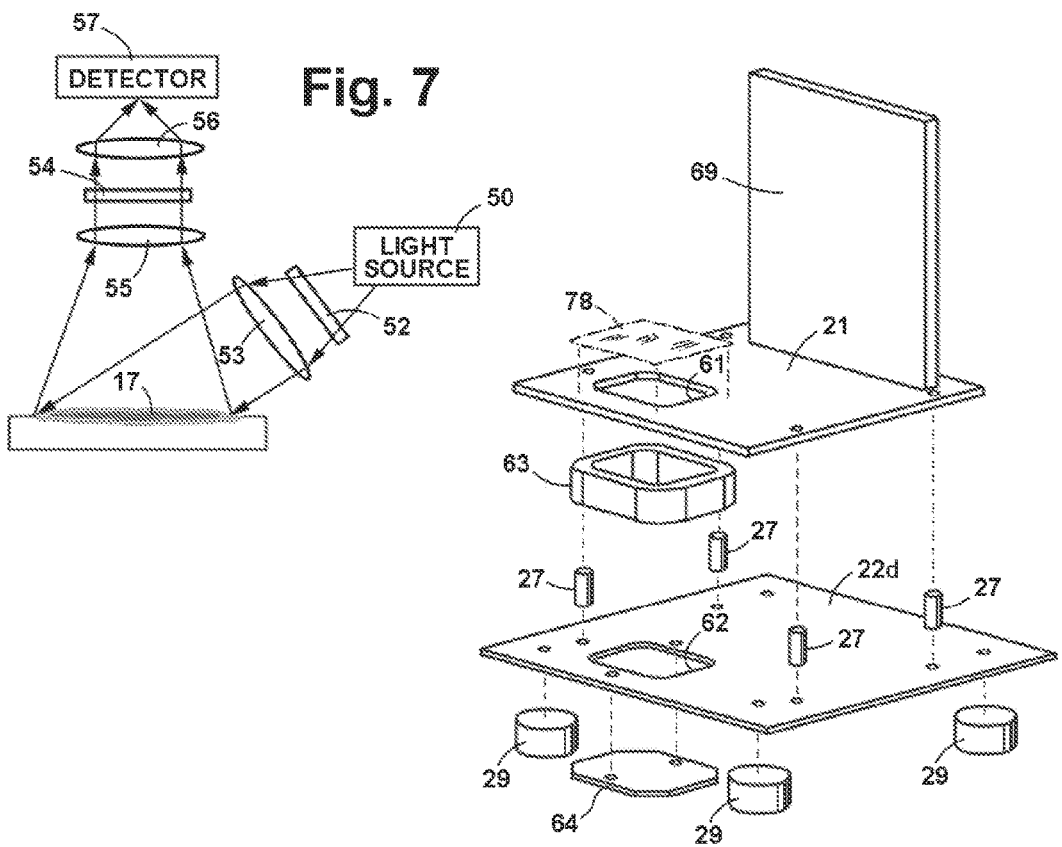
Fig. 7
Fig. 8

ANALYTE DETECTOR AND METHOD

BACKGROUND OF THE INVENTION

Field of Invention

This invention pertains generally to the detection of pesticides and other analytes and, more particularly, to a portable, handheld instrument and method which are particularly suitable for detecting pesticides on produce.

Related Art

Organic farming has been one of the fastest growing segments of American agriculture in recent years, and many people prefer organic produce because of its superior taste and quality. Organic farmers are not allowed to use synthetic pesticides or fertilizers, and organically grown produce contains significantly lower levels of pesticide residues than conventionally grown produce. With its more stringent growing requirements, popularity among consumers, and relatively limited availability, organic produce generally commands a higher price than other fruits and vegetables.

Produce is currently checked for pesticide residue by sending a sample of the fresh produce to a laboratory for analysis, which often requires several days to obtain a result.

In conventional lab testing, the mass of the sample is measured, the sample is ground up, and the mass of the analyte is then measured as a fraction of the sample mass, in parts per million (PPM). In another type of measurement known as dislodgeable foliar residue (DFR) measurements, the analyte is washed off the sample with a solvent, the mass of analyte is measured in the solvent, and the concentration is reported in mass per unit area of sample. DFR measurements are normally used in testing for worker safety, rather than safety for human consumption.

Heretofore, there have been some attempts to provide portable instruments for checking produce for the presence of pesticide residue through fluorescence spectroscopy in the field using an aqueous sample which is placed in a cuvette and analyzed in a spectrometer. While such instruments avoid the need to send the sample to a laboratory, the use of the aqueous sample is still time consuming and cumbersome.

U.S. Pat. Nos. 7,304,741 and 7,400,405 disclose portable, self-contained instruments which can be pointed at a target to detect the presence of pesticide residue instantly and without contact with the produce. Those instruments can be used in the field and in other locations to determine pesticide content.

OBJECTS AND SUMMARY OF THE INVENTION

It is, in general, an object of the invention to provide a new and improved instrument and method for detecting analytes.

Another object of the invention is to provide an instrument and method of the above character which are particularly suitable for detecting pesticides on produce.

These and other objects are achieved in accordance with the invention by providing an instrument having a housing which is substantially impervious to light, mounting a sample to be tested on a cassette and inserting the cassette into the housing, and directing light from a source within the housing toward the sample to induce fluorescent emission from analyte on the sample. Fluorescent emissions from the sample are monitored with a detector within the housing to detect emissions having a spectral content characteristic of an analyte to be detected. Data from the detector is processed, and information based on the processed data is displayed. In some embodiments, the instrument is calibrated with data from a reference sample of known concentration or density. The detector measures the analyte in units of mass per unit area, and in some embodiments the mass per unit area data is converted to units of concentration or density of the analyte in the sample.

BRIEF DESCRIPTION OF THE DRAWINGS

FIG. 2 is an exploded isometric view of the cassette in the embodiment of FIG. 1 being loaded with a sample to be examined.

FIG. 3 is an isometric view of the cassette of FIG. 2 in a closed position with the sample in it.

FIG. 4 is a vertical sectional view of the embodiment of FIG. 1, taken behind the front panel and the bezel, with the cassette removed.

FIG. 5 is a cross-sectional view taken along line 5-5 in FIG. 4.

FIG. 6 is a cross-sectional view taken along line 6-6 in FIG. 5.

FIG. 7 is an optical diagram of the cassette reader in the embodiment of FIG. 1.

FIG. 8 is an exploded isometric view of the chassis, bottom cover, and related elements in the embodiment of FIG. 1.

DETAILED DESCRIPTION

Figure 1:
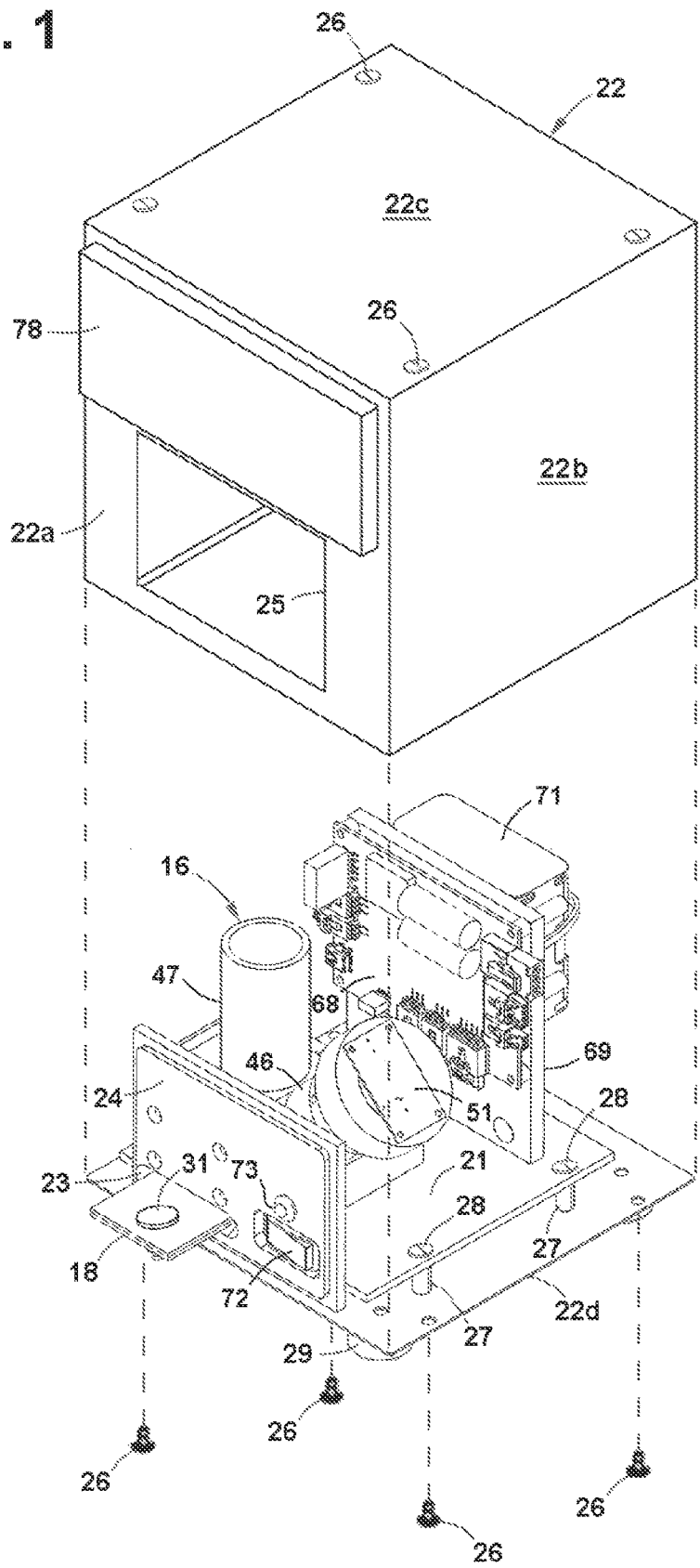
FIG. 1 is an isometric view, partly exploded, of one embodiment of an analyte detector incorporating the invention.

In the embodiment of FIG. 1, the instrument has a detector system or reader 16 for detecting pesticides and other analytes on a specimen 17 mounted in a cassette or cartridge 18 which is inserted into the reader. The reader is mounted on a chassis 21 within an enclosure 22 that is substantially impervious to light so that ambient light will not affect the readings of the detector. The cassette is inserted into the reader through an opening or slot 23 in a faceplate or bezel 24 which is affixed to one side of the reader and projects through an opening 25 in the front panel 22a of the enclosure.

The enclosure is generally cubical in shape with square side walls 22b and removable top and bottom covers 22c, 22d which are attached to the body of the enclosure by fasteners such as mounting screws 26. The chassis is mounted on and spaced above the bottom cover by spacers 27, with the chassis and the bottom cover being secured to the spacers by screws 28 or other suitable fasteners. The instrument is designed for portability, e.g., to be held in the hand and carried about, and in one present embodiment, the enclosure measures approximately 6 inches on each side. Mounting feet 29 are attached to the lower side of bottom cover 22d to protect surfaces on which the instrument is placed as well as preventing the instrument from sliding about those surfaces.

As best seen in FIGS. 2 and 3, the cassette has an upper panel 18a and a lower panel 18b joined together by hinges 18c. In the embodiment illustrated, the two panels and the hinges are formed as a unitary structure by cutting them from a sheet of polypropylene or another thermoplastic polymer such as polycarbonate or polystyrene. This material is relatively stiff, and the unitary structure is thermo formed to a closed position with the upper panel overlying the lower panel. Alternately, if desired, the cassette can be formed by injection molding or other suitable processes.

The two panels are rectangular in shape and are held in the closed position by a rivet 31 which passes through aligned openings 32a, 32b toward the ends of the panels opposite the hinges. Relatively large circular viewing windows or openings 33a, 33b are formed in the central area of the panels, and locating holes 34a, 34b are formed near the hinges. In the embodiment illustrated, the openings are centered on the longitudinal centerline or axis 36 of the panels, and the viewing windows are tangent to the lateral centerline or axis 37. With the panels in the closed position, the corresponding openings in the two panels are aligned with each other.

The specimen 17 is positioned between the two panels in alignment with viewing windows 33a, 33b and is held in place by pressure from the two panels. The specimen can, for example, be a leaf from produce such as spinach or lettuce, a slice taken from another fruit or vegetable, or any other substrate on which a pesticide or other analyte is to be detected and/or measured. With the cassette in an open position, the specimen is placed on the lower panel above window 33b. The two panels are then closed together against the specimen, and the rivet is inserted to lock the panels in the closed position and hold the specimen in place. Any portion of the specimen extending beyond the edges of the panels can be trimmed away.

Since the two panels are identical, the cassette can be inserted into the reader with either side facing up, and the analyte on either or both sides of the specimen can be measured. The ability to test both sides can be important in situations such as where only one side of the specimen has been exposed to the analyte or where the total analyte on both sides of the specimen needs to be determined. Alternatively, the reader can be provided with additional components for measuring the analyte on both sides of the specimen simultaneously.

The reader has a body or block 39 with a cavity 40 into which the cassette is inserted for analysis of the specimen. The cavity is aligned with the opening or slot 23 in bezel 24 and, in the embodiment illustrated, is formed by a slot 41 which opens through the lower side of the block and by the upper side of the chassis 21 on which the reader is mounted. The height and width of the cavity are slightly greater than the corresponding dimensions of the cassette so that the cassette is readily slid into and out of the cavity and, when fully inserted, blocks the opening so that ambient light cannot enter the enclosure and affect the readings.

The cassette is held in place in the reader by a releasable latch or detent assembly 42 comprising a body 43 that is threadedly mounted in the reader block and has an axial bore 43a that is open at its lower end. A detent ball 44 is mounted in the bore for movement into and out of the cavity formed by locating holes 34a, 34b when the cassette is inserted into and removed from the reader cavity. The ball is urged in a downward direction toward the cassette by a compression spring 45 in the bore above the ball.

As the cassette is pushed into the reader, the force exerted on the ball by the cassette lifts the ball and allows the cassette to pass beneath the ball until the ball drops into the cavity formed by the locating holes in the cassette, at which point the cassette is locked in position, with the spring urging the ball into engagement with the walls of the holes. When the cassette is pulled out of the reader, the force exerted on the ball by the walls of the holes lifts the ball against the spring, allowing the cassette to pass beneath the ball.

Light source and detector barrels 46, 47 are mounted in intersecting bores 48, 49 in the reader block. In the embodiment illustrated, detector barrel and bore extend vertically, and the light source barrel and bore extend at an angle of 45 degrees to the vertical, with the centerlines of the bores intersecting at the center of specimen windows in the cassette.

The reader includes a light source 50 at the outer end of barrel 46 for generating light which is directed onto the specimen to produce fluorescent emission having a spectral content characteristic of the material that is emitting it. In one presently preferred embodiment, the light source is a xenon flashlamp mounted on a circuit board 51 with a reflector (not shown) for directing light from the flashlamp toward the specimen. Other types of light sources such as ultraviolet LEDs or a mercury vapor lamp can be utilized, if desired.

A UV filter 52 is mounted in barrel 46 between the light source and specimen. This filter is selected to pass light at a wavelength that produces the maximum fluorescent emission from the pesticide or other analyte to be detected. A lens 53 is mounted in the barrel between the UV filter and the specimen for focusing light passing through the filter on the specimen. A second UV filter 54 and a pair of lenses 55, 56 are mounted in barrel 47 between the specimen and a UV detector 57 at the outer end of the barrel. That filter is chosen to selectively pass emissions having a spectral content which is characteristic of the pesticide or analyte to be detected, and the lenses focus those emissions on the detector.

Carbaryl pesticide (1-naphthyl methylcarbamate), for example, has an optimum excitation wavelength of about 270 nm and an emissions peak around 330 nm, and filters 52 and 54 have passbands centered at those wavelengths when carbaryl is to be detected.

Other pesticides or analytes that may also be present on the specimen may emit light at slightly different wavelengths. To prevent such analytes from producing erroneous readings, techniques such as multiple filter sets and spectral unmixing can be employed in measuring the fluorescence to increase the specificity to a particular analyte and provide more accurate results. Such techniques can also provide measurements for multiple analytes such as other carbamate pesticides that have different fluorescence excitation spectra and/or different emission spectra.

Multiple filter sets can be implemented, for example, by mounting a plurality of filters in pairs on a wheel or other suitable carrier which can be moved to bring the filters for the desired analyte into registration with the light source and detector, as described in greater detail in U.S. Pat. Nos. 7,304,741 and 7,400,405.

Spectral unmixing is particularly useful when a plurality of fluorescent analytes have overlapping emission spectra and the measured signals for each filter set or channel have cross-talk or components from some or all of the analytes being measured. Spectral unmixing is a well known technique in which the amounts of emissions passing through a filter from analytes other than the one to be measured are subtracted from the total amount of emissions passing through the filter so that the final result includes only the emissions from the analyte being measured.

A port 59 is provided for cleaning out the detector assembly or reader to remove debris from the specimens which might otherwise accumulate over time and possibly cause erroneous readings. The port includes openings 61, 62 in chassis 21 and the bottom cover 22d of the enclosure directly beneath the window area of the cassettes, with a gasket 63 surrounding the openings and bridging the gap between the bottom cover and the chassis. An access plate or door 64 is removably secured to the under side of the bottom cover by thumbscrews 66, 66 which are threadedly received in block 39.

The detector assembly or reader can be cleaned periodically by removing the cassette and the access plate and, with the unit right-side-up, gently shaking out any loose debris. Thereafter, the unit can be turned up-side-down and inspected visually, and any remaining debris in the detector assembly or on the lenses can be removed with plastic tweezers or alcohol-soaked swabs as needed.

Electronic circuitry for controlling the light source and processing signals from the detector is located on a circuit board 68 mounted on one side of an upright support 69 affixed to the chassis 21, and batteries for powering the instrument are mounted in a battery pack 71 on the other side of the support. A power switch 72 and a power indicator light 73 are located on the front panel or bezel 24 and are accessible outside the enclosure.

Figure 9:
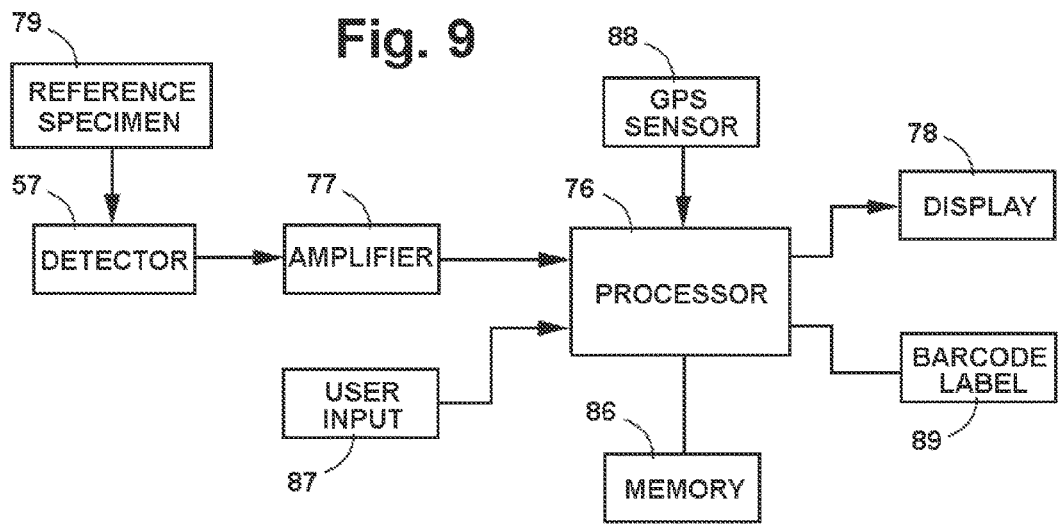
FIG. 9 is a simplified block diagram of the embodiment of FIG. 1.

As illustrated in FIG. 9, the processing circuitry includes a processor 76 which receives data and instructions from detector 57 and other sources and processes the data in accordance with the instructions to provide information about the pesticide or other analyte on the specimen. Signals from the detector are amplified and converted to digital form for the processor by an amplifier and converter stage 77, and the information from the processor is applied to a display 78.

The display can, for example, be a touchscreen mounted on the front panel of the instrument, as illustrated in FIG. 1. In addition to displaying information such as the results of measurements made with the instrument, the touchscreen also serves as an interface through which data and commands are entered. If desired, other types of input devices and displays can be employed in the instrument, including keypads and a liquid crystal displays. Alternatively, the instrument can be connected externally to a laptop computer, cell phone, tablet, or other device having input, processing, and display capabilities.

Since fluorescent measurements are inherently relative measurements, the absolute fluorescence signal from any specimen or sample will vary with the intensity of illumination and the sensitivity of the detector, both of which can vary during the operation of the instrument due to age or environmental conditions. To prevent such variations from affecting the accuracy of the readings, the instrument is calibrated periodically.

Factory calibration is typically done with a series of reference analyte samples ranging between high and low concentration levels. The signal is measured for each known concentration, and stored in the reader's memory to provide what is commonly called a standard curve. Then, when unknown samples are measured, the data is interpolated into the standard curve to determine the concentration of the unknown analyte. Factory calibration is generally done only once at the time the instrument is manufactured.

In addition, a calibration reference sample 79 is used periodically to test the instrument for proper operation and to correct for instrument changes, such as reduced light output from an aging flashlamp or dust accumulation on the optics. The calibrator sample is measured periodically, and the instrument's standard curve can be adjusted in memory, if necessary, to yield the correct concentration reading for the calibration sample. That sample can contain the actual analyte, or it can be another material such as one which gives a fluorescence signal that is equivalent to a certain amount of analyte.

In the embodiment illustrated, calibration samples are mounted in special calibration cassettes which are inserted into the reader periodically to check and calibrate the performance of the reader. These cassettes do not need to have a very long lifetime and can be replaced periodically.

In another embodiment, a calibration reference sample is installed in every cassette along with the specimen to be analyzed. Thus, for example, as shown in broken lines in FIG. 2, a reference sample 79 and a specimen 17 can be placed back-to-back in the cassette in alignment with the viewing windows. With the calibration sample in the cassette, calibration can be performed every time a measurement is made, simply by turning the cassette over.

Figure 10:
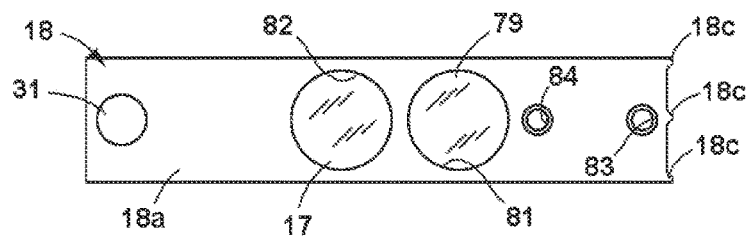
FIG. 10 is a top plan view of a cassette having both a calibration reference sample and a sample to be tested.

If desired, the cassette can have both a calibration sample and a test sample which are accessible from the same side of the cassette. Thus, for example, as shown in FIG. 10, a calibration sample window 81 and a test sample window 82 are spaced apart along the centerline of the cassette, and a separate detent opening 83, 84 is provided for each of the windows. In use, the cassette is initially inserted only partially into the reader with detent ball 44 engaging detent opening 83 and calibration sample 79 in position to be read. Once the calibration measurement is made, the cassette is pushed further into the reader until the detent ball engages the second detent opening 84 and test sample 17 is in position to be read.

In other embodiments, a replaceable calibration sample is included as a permanent part of the instrument itself. Thus, for example, as shown in FIG. 8, a calibration sample 79 can be mounted on the upper side of chassis 21 over opening 61. When the cassette is in place, it covers the calibration sample and shields it from the reader, but when the cassette is removed, the calibration sample is exposed and can be accessed by the reader.

Means is also included for comparing the amount of analyte detected on a specimen with a threshold level and indicating whether the measured amount is above or below the threshold. This means includes a memory 86 in which threshold data for different analytes is stored and a user interface 87 such as touchscreen 78 through which the type of specimen to be analyzed is selected. Federal regulations provide pesticide tolerances for different types of produce and other food commodities. Under those regulations, spinach, for example, has a carbaryl tolerance of 22 parts per million (ppm), while lettuce has a tolerance of 10 ppm for carbaryl. With different threshold levels for a given analyte on different types of specimens, the stored data includes threshold data for each pesticide or analyte on the different types of produce or specimens.

Direct fluorescence detection of carbaryl and other analytes, as done by the reader in the present invention, gives results which are proportional to the mass of the analyte detected, and the processor is programmed to convert measurements of mass per unit area to the ratio of the analyte mass to the mass of the sample in units of parts per million (ppm). In order to make that conversion, the mass of the sample must be determined.

In one example, it was determined that an average spinach leaf has a thickness of about 0.7 mm, or 0.07 cm, and a density of about 0.9 g/ml. Thus, a 1 cm by 1 cm specimen would have a volume and mass given by the following relationships:

$$\text{Volume} = 1 \text{ cm}^2 \times 0.07 \text{ cm} = 0.07 \text{ cm}^3 = 0.07 \text{ ml}$$

Mass=0.07 ml×0.9 g/ml=0.063 grams

Assuming a direct fluorescence measurement of 5.0 µg/cm², the mass ratio of the analyte and the sample is $$\frac{5.0 \times 10^{-6} \text{ g carbaryl}}{0.063 \text{ g sample}} \times 10^6 = 79.4 \text{ ppm}$$

Thus, for an average spinach leaf, the result in ppm is approximately 16 times the result in µg/cm², and the measured mass per unit area can be converted to the mass ratio simply by multiplying the mass per unit area by 16.

When the user selects the type of analyte to be measured, the processor retrieves the threshold level for the particular analyte and the type of specimen from the memory, compares the measured amount with the threshold level, and conditions the display to provide a visual display as to whether the measured amount is above or below the threshold level. If the measured amount is below the threshold level, the display might, for example, display a green light, indicating that the specimen has passed the test and meets the federal standard. Similarly, if the measured amount is above the threshold level, a red light on the display will indicate that the specimen has failed the test and does not meet the standard.

The processor also receives an input from a global positioning sensor (GPS) 88 corresponding to geographic location of the instrument. By checking the GPS signal when a measurement is made, the processor is able to store geo-tagged measurement data in memory 86. When used in combination with software or web services that provide mapping or Geographic Information Services, this data can add value in a number of ways including, for example, detecting pesticide drift from one field to another. With the GPS system, the instrument can take separate measurements for different coordinates in a field, including, for example, the date and time of the measurement, the type of crop, the results of the measurement, the time of exposure, the time of spraying, and the type of spraying, e.g. aerial, by tractor, or a handheld wand.

In some embodiments, the processor also receives data from a barcode label 89 affixed to the cassette. The barcode contains information such as a unique serial number, a passcode, and lot-specific calibration data. The instrument can use this data in storing information such as the type and amount of analyte on the specimen, the date, time, and location of the measurement, identification of the person making the measurement, and/or other information about the measurement or the specimen. That information can then be printed out on another barcode label or document that is shipped with the product tested.

The instrument can be coupled with a cell phone or computer linked to the internet or another computer network to distribute information about the test results and/or the sample among farmers, governmental agencies, packers, shippers, retailers, and the like, and in some applications, remote users can conduct tests with the instrument through their cell phones or computers.

The instrument can used by growers, packers, shippers, wholesalers, and retailers alike, as well as by local, state, and federal inspectors, and it provides an easy way for those in the supply chain to check the product they receive for excess pesticide residue and refer it back to the person before them if there is a problem. If desired, each one in the chain can record his readings, for example by posting them on the cartons and/or on the internet.

The unique serial number and passcode make it possible to identify where readings come from, and that can be very important when expensive shipments of produce are rejected as having too much pesticide residue. The passcode linked to the test results, the GPS coordinates, and the date is a unique function of the instrument by which it can be identified. This can have added value if the pass code follows the metadata to an online data base, allowing customers to monitor trends and employee performance.

The invention has a number of important features and advantages. It provides a highly portable, self-contained, battery powered instrument which can detect the presence of pesticide residue and other analytes. It can be used in the field and in other locations to determine pesticide content on organically grown produce as well as on produce grown by other means.

It is apparent from the foregoing that a new and improved analyte detector and method have been provided. While only certain presently preferred embodiments have been described in detail, as will be apparent to those familiar with the art, certain changes and modifications can be made without departing from the scope of the invention as defined by the following claims.

The invention claimed is:

1. A portable instrument for detecting an analyte on a specimen, comprising:
    a housing which is substantially impervious to light,
    a cassette which carries the specimen and is removably inserted into the housing,
    a light source within the housing for directing light toward the specimen to induce fluorescent emission from analyte on the specimen,
    a detector within the housing responsive to fluorescent emissions having a spectral content characteristic of the analyte to be detected and providing data corresponding to the mass of analyte detected per unit area on the specimen,
    means for processing data from the detector by multiplying the volume per unit area of the specimen by the density of the specimen to determine the mass per unit area of the specimen and dividing the mass per unit area of the analyte detected on the specimen by the mass per unit area of the specimen to determine the mass ratio or concentration of the analyte and specimen, and
    a display which is responsive to the processed data and visible externally of the housing for displaying information about the analyte on the specimen.

2. The instrument of claim 1 including a filter positioned between the light source and the specimen for selectively passing light of a wavelength that excites fluorescence of the analyte on the specimen.

3. The instrument of claim 1 including a filter positioned between the specimen and the detector for selectively passing emissions having a spectral content characteristic of the analyte to be detected.

4. The instrument of claim 1 including a battery within the housing for powering the light source, the means for processing the data, and the display.

5. The instrument of claim 1 wherein the analyte is a pesticide, and the specimen is selected from the group consisting of lettuce leaves, spinach leaves, and samples of other produce.

6. The instrument of claim 1 including a reference sample for use in calibrating data from measurements of the analyte on the specimen.

7. The instrument of claim 6 wherein the reference sample is permanently installed within the housing.

8. The instrument of claim 6 wherein the reference sample is mounted on a calibration cassette which can be inserted into the housing in place of the cassette which carries the specimen.

9. The instrument of claim 6 wherein the reference sample is mounted on the cassette with the specimen.

10. The instrument of claim 1 wherein the means for processing data from the detector includes data processing circuitry within the housing.

11. The instrument of claim 1 wherein the means for processing the data includes means for comparing the amount of analyte detected with a predetermined threshold level, and the display includes means for indicating whether the amount detected is above or below the threshold level.

12. The instrument of claim 11 including means for storing threshold levels for an analyte on a plurality of different specimens, and means for comparing the amount of analyte detected with the threshold level for a selected one of the specimens.

13. The instrument of claim 1 including a global positioning device for providing data corresponding to the location of the instrument when measurements are taken, and means for tagging measurement data with the location data.

14. The instrument of claim 1 wherein the housing includes a cleaning port with a removable closure which provides access to the region where the specimen is inserted.

15. A method of detecting an analyte on a specimen, comprising the steps of:
inserting the specimen into a housing which is substantially impervious to light,
directing light from a source within the housing toward the specimen to induce fluorescent emission from analyte on the specimen,
monitoring fluorescent emissions from the specimen with a detector within the housing to detect emissions having a spectral content characteristic of the analyte to be detected,
storing threshold levels for an analyte on a plurality of different specimens,
comparing the amount of analyte detected with the threshold level for a selected one of the specimens, and
indicating whether the amount detected is above or below the threshold level.

16. The method of claim 15 including the step of filtering light passing from the source to the specimen to selectively pass light of a wavelength that excites fluorescence of the analyte on the specimen.

17. The method of claim 15 including the step of filtering emissions between the specimen and the detector to selectively pass emissions having a spectral content characteristic of the pesticide to be detected.

18. The method of claim 15 including the step of supplying power to the light source, processing circuitry within the housing, and the display from a battery within the housing.

19. The method of claim 15 wherein the analyte is a pesticide, and the specimen is selected from the group consisting of lettuce leaves, spinach leaves, and samples of other produce.

20. The method of claim 15 including the steps of monitoring a reference sample, and calibrating data from measurements of the analyte on the specimen in accordance with data from the reference sample.

21. The method of claim 20 including the steps of periodically removing the cassette with the specimen from the housing and inserting a calibration cassette with the reference sample into the housing in place of the cassette with the specimen.

22. The method of claim 20 wherein the reference sample is mounted on the cassette with the specimen and inserted into the housing with the specimen.

23. The method of claim 15 including the step of converting data from the detector from units of mass per unit area to the mass ratio or concentration of the analyte and specimen.

24. The method of claim 15 including the steps of providing global positioning data corresponding to the location of the instrument when measurements are taken, and tagging measurement data with the location data.

25. A method of detecting an analyte on a specimen, comprising the steps of:
inserting the specimen into a housing which is substantially impervious to light,
directing light from a source within the housing toward the specimen to induce fluorescent emission from analyte on the specimen,
monitoring fluorescent emissions from the specimen with a detector within the housing to detect emissions having a spectral content characteristic of the analyte to be detected,
multiplying the volume per unit area of the specimen by the density of the specimen to determine the mass per unit area of the specimen, and
dividing the mass per unit area of the analyte detected on the specimen by the mass per unit area of the specimen to determine the mass ratio or concentration of the analyte and specimen.

26. The method of claim 25 including the steps of comparing the amount of analyte detected on the specimen with a predetermined threshold level, and indicating whether the amount detected is above or below the threshold level.

* * * * *